United States Patent [19]
Pugliese

[11] Patent Number: 6,153,207
[45] Date of Patent: Nov. 28, 2000

[54] ANTI-CELLULITE PANTYHOSE

[76] Inventor: Peter T. Pugliese, P.O. Box 250, Bernville, Pa. 19506

[21] Appl. No.: 09/035,315

[22] Filed: Mar. 5, 1998

[51] Int. Cl.[7] .................................................. A01N 25/34
[52] U.S. Cl. ..................... 424/402; 424/78.02; 424/448; 424/486; 428/288; 428/290; 428/342
[58] Field of Search ............................... 424/402, 78.03, 424/448, 486; 2/2, 243; 428/288, 290, 342

[56] References Cited

U.S. PATENT DOCUMENTS

| | | | |
|---|---|---|---|
| 4,859,527 | 8/1989 | DiStefano | 428/288 |
| 5,611,885 | 3/1997 | Hansen et al. | 156/326 |
| 5,744,453 | 4/1998 | Mintz et al. | 514/26 |
| 5,928,958 | 7/1999 | Pilgrimm | 436/526 |

Primary Examiner—Jose' G. Dees
Assistant Examiner—Kathryne E. Shelborne

[57] ABSTRACT

A garment for treating the skin, a method of making the garment and a method of using the garment to treat the skin, made of garment material, in particular hose material to be worn tightly against the skin, which has a multiplicity of durable chemical bonding sites. The durable sites which are preferably of the type to make covalent bonds, are bound to binding molecules which form chemical hooks for the garment material. Each of the chemical hooks has one or more semi-durable chemical bonding sites of the type which can chemically bond an active ingredient molecule to the binding agent but which is broken in the presence of skin conditions which are normal such as normal skin pH, normal skin moisture and normal skin heat generated both by body heat and the heat of friction of the garment rubbing against the skin. Active ingredient molecules such as molecules of theophylline or theophylline complexes are bound to the binding agent and are released to the skin when the garment is worn.

23 Claims, 5 Drawing Sheets

ANTI-CELLULITE PANTYHOSE

FIELD AND BACKGROUND OF THE INVENTION

The present invention relates, in general, to skin treatments using hose or other garments made of hose material that is worn tightly on the skin, and, in particular, to a new and useful product, method of making the product and treatment method using the product, which first chemically binds an active ingredient to the hose material by semi-duralite bond, and then releases the active ingredient to the skin while the hose material is worn by breaking the semi-durable bond using skin conditioners such as pH, moisture and/or heat. In the preferred embodiment of the invention the hose material is nylon, the active ingredient is theophylline and the treatment is for cellulite.

Cellulite is an accumulation of fatty tissue in the upper layers of the skin which is manifested as a "mattress button" defect in the skin. It is known that a class of physiological ingredients known as xanthines are capable of reducing fatty tissue in underlying skin if applied topically. The most common xanthines are caffeine, theophylline and theobromine. Theophylline is the most common xanthine used in the treatment of cellulite.

U.S. Pat. No. 4,288,433 to Koulbanis et al. teaches using xanthine compounds, of which theophylline is one (caffeine is another), to treat cellulite. The xanthine compounds are combined with other chemical groups, or radicals, such as alkyls, allyls, propynols and cyclohexyls.

A composition containing xanthine compounds mixed with alpha hydroxy acid and/or phytic acid for applying to cellulite-affected areas is the subject of U.S. Pat. Nos. 5,523,090 and 5,536,499, both to Znaiden et al. The compound is disclosed for direct application to a user's skin.

U.S. Pat. No. 5,051,449 to Kligman et al. uses retinoid compounds applied directly to the skin to treat cellulite. The retinoid compound is preferably retinoic acid mixed in a commercial lotion.

A heated massager for use in treating cellulite is disclosed in U.S. Pat. No. 4,086,922 to Henderson.

Other patents disclose the use of theophylline compounds to treat various medical disorders, such as U.S. Pat. No. 3,962,243 to Roldan et al., which teaches the use of mepyramine theophylline acetate to treat bronchial disorders and relieve the effects of histamine poisoning. Mepyramine is combined with a suspension of 7-theophylline acetic acid to form the claimed compound of Roldan '243.

A stable form of a theophylline compound is disclosed in U.S. Pat. No. 4,085,214 to Higuchi et al. Higuchi '214 combines theophylline with a phenylalkenyl group having 2–8 carbons in the alkenyl portion to provide a theophylline drug useful in treating asthma.

U.S. Pat. No. 4,241,682 to Konstandt discloses coating boats with polyethylenimine solutions to improve the movement of the boats through water.

Patents on pantyhose or articles of clothing having cosmetic treatment properties include U.S. Pat. No. 4,152,784 to McGalliard for a nylon hose treated with a microencapsulated depilatory. The depilatory is released to a wearer's skin while the hose are worn when microcapsules are ruptured by contact with hair stubble. EP 009,499 to McGalliard corresponds to U.S. Pat. No. 4,152,784.

A method of treating cellulite by wrapping the affected portions of a persons' body with a body wrap soaked in a mineral solution and then exercising while wearing a vinyl exercise suit is taught by U.S. Pat. No. 4,829,987 to Stewart. The mineral solutions of Stewart '987 must be warmed and leave a residue on the person's body when done. The mineral solutions are more fully discussed in a book cited in the patent. The mineral solutions appear to be very different from the THA compounds of the invention.

A sock having reduced friction with a wearer's foot due to coating or impregnating, among other things, with a fluoropolymer is covered by U.S. Pat. No. 5,575,012 to Fox et al.

U.S. Pat. No. 5,051,256 to Barnes teaches an iodine compound which may be linked to Nylon-4 to provide an anti-bacterial fabric having an extended time-release of iodine as the active agent.

U.S. Pat. No. 5,156,843 to Leong et al. is for a fabric impregnated with coated microspheres to provide a controlled, time-release of the material used to coat the microspheres.

A transdermal delivery patch for a drug having the active substance microencapsulated and combined with a polymer skin enhancer is disclosed by U.S. Pat. No. 5,614,212 to D'Angelo et al. The skin enhancer is preferably polyvinylpyrrolidone, or PVP.

British Patent Specification GB 1,581,586 to Yamauchi discloses a stocking or panty hose having a solid sanitary composition which includes a water-insoluble resin binder having a metal dispersed within the binder.

GB 1,361,289 to Alza Corp. and European Application EP 436,729 Kanebo Ltd. both teach treatment compositions using microcapsules initially attached to a bandage or stocking to deliver the active ingredients to a person's skin.

EP 174,108 to Jost discloses a porous, two-layer polymeric foam patch for transdermally delivering medicine to a person.

Italian Patent 1,191,244 to Alza Corp. corresponds to UK Patent 1,361,289 and to U.S. Pat. No. 4,435,180. These patents teach a treatment composition using microcapsules initially attached to a stocking to deliver the active ingredients to a person's skin. The stocking provides a compressive force against the person's skin to make good contact between the composition and the skin.

Italian Patent 951,409 to Eurand SpA discloses a method of applying microcapsules to textiles, such as for underwear or linens. The microcapsules contain a fragrance.

An injectable composition containing theophylline is taught by Italian Patent 1,093,259 in the name of Holzmann.

Italian Patents 1,191,962 to Malesci, 1,217,516 to Caroprese, 1,258,343 to Comi and 1,263,754 each disclose compositions for treating cellulite. The compositions of these patents are different from the inventive composition.

SUMMARY OF THE INVENTION

It has been found that compliance and time of application of cellulite reduction agents are critical to an effectiveness of the treatment. The present invention provides a product, method of making the product and treatment using the product which advances compliance and the extended time of treatment in an automatic manner by incorporating the active treatment ingredient into an article of closely fitting clothing, that is a garment, and in particular, hose.

A preferred embodiment of the present invention comprises a nylon pantyhose or stocking having polyethylenimine (PEI) permanently chemically bound by durable chemical bonds, to the nylon, and tonically bonded by a semi-durable chemical bond to theophylline acetate (THA), the active ingredient. The PEI provides a durable chemical hook from the nylon to the THA that increases the number of available ionic bond locations by a factor of 3.

For the purpose of this disclosure, a durable chemical bond or binding site is one which will not be broken by skin conditions such as skin pH (about 5.5), skin moisture or skin heat due to friction or body heat. The durable bond also will not be broken due to ordinary washing.

The ionic or semi-durable bond requires a low pH (less than 5 pH). The THA may be completed with a compound known as SILANTRIOL, which is known to improve the passage of chemicals through human skin.

The ionic bond is here referred to as a semi-durable which is broken by one or more skin conditions selected from skin pH, skin moisture, and/or skin heat (due to friction or body heat). The semi-durable bond is not broken, however, by washing the garment in a usual way (i.e. with detergent, warm water and agitation).

When the pantyhose are worn, the THA is gradually released to the wearer's skin from the ionic bond, and the pantyhose, due to a combination of three factors: pH increased above 5 by contact with wearer's skin (skin pH is about 5.5); moisture from wearer's skin; and body and friction heat (collectively skin heat). Over time, the THA has the effect of reducing cellulite. The pantyhose may be "recharged" by soaking it in a solution of THA.

The pantyhose are chemically treated in a multistep process to bond the PEI and THA to the pantyhose. First, the pantyhose are washed twice in distilled water and damp dried. Then, the pantyhose are immersed in a solution of PEI for 30 minutes with constant agitation. Following immersion, the pantyhose are washed twice in deionized water and damp dried. The PEI is now permanently bonded with the nylon of the pantyhose, creating the chemical hook to tonically bond THA or other substances.

Meanwhile, the THA-SILANTRIOL complex is prepared by incrementally adding SILANTRIOL to a solution of THA at a pH of 5.5. The pH of the THA-SILANTRIOL complex is then reduced below 5 prior to the next step.

To ionically bond the THA-SILANTRIOL complex to the PEI, the pantyhose with the PEI chemical hook are immersed in a solution of the THA-SILANTRIOL complex for 3 hours with constant agitation. The pantyhose are then washed twice in deionized water and dried.

The resulting chemically treated pantyhose may be stored in the dry state indefinitely without decomposition of any of the compounds or chemical bonds.

Accordingly an object of the present invention is to provide a garment for treating the skin of a wearer with an active ingredient, comprising a garment material having a multiplicity of durable chemical binding sites, a binding agent molecule chemically bound to each of the durable binding sites, each binding agent molecule having at least one semi-durable chemical binding site which can be broken by at least one of skin pH, skin moisture and skin heat, and an active ingredient molecule bound to each semi-durable chemical binding site so that the active ingredient is chemically bound to the garment when the garment is not worn and so that the active ingredient is released to the skin when the garment is worn and the semi-durable binding sites are exposed to at least one of skin pH, skin moisture and skin heat to break bonds between the active ingredient molecules and the binding agent molecules.

Another object of the present invention is to provide a method of making such a garment and a method of treating the skin with such a garment.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

Figure 1:
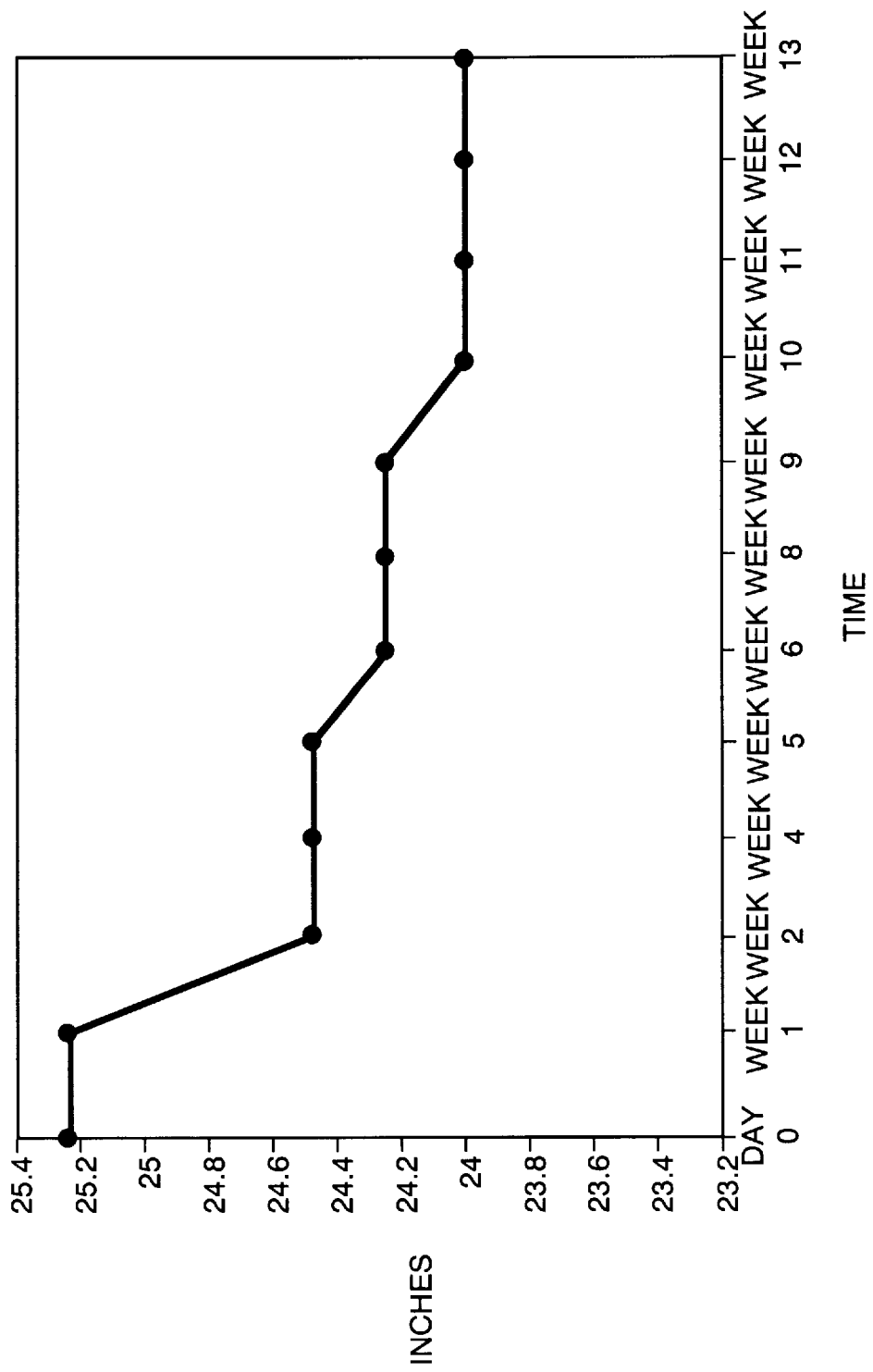
FIG. 1 is a graph illustrating the circumference of the left thigh of a test subject, against time.

The product of the present invention is a garment which is made of garment material of the type meant to be worn closely against the skin of a wearer, in particular hose, pantyhose, other undergarments or similar garments, made of a wide variety of garment material, again in particular hose material which is meant to fit closely against the skin, such as natural, synthetic and semi-synthetic materials including cotton (a cellulose fiber made from certain plants), silk (a scleroprotein of fibroin, containing glycine and alanine, secreted by the silkworm), rayon (a semi-synthetic fibrous cellulose), Dacron (a DuPont trademark for a polyester fiber made from polyethylene terephthalate) and nylon (polyamide polymers characterized by the presence of an amide group-CONH). The requirement of the present invention is that, regardless of the garment material selected, a durable chemical binding site must be present, such as the regular amide groups along the nylon chain or the regular ester locations along the Dacron polyester filament chain. Similar durable chemical bond sites can be identified and utilized in the case of other garment fibers such as rayon, silk and cotton. The preferred durable bond is a covalent bond. The importance for the invention is that a binding agent molecule be chemically bonded at one of these durable chemical binding sites by a durable chemical bonds and that the binding agent itself provide one or more semi-durable bond such as an ionic bond, for attaching the active ingredient molecules in a matter which can be broken in the presence of normal skin conditions such as skin pH, skin moisture, and/or skin heat including body heat and heat due to frictional movement of the garment against the skin. The binding agent can be thought of as the hook which attaches the active ingredient to the garment in a way that the active ingredient can be disconnected by breaking the semi-durable bond due to the presence of one or more of the skin conditions, to release the active ingredient to the skin. To the knowledge of the applicant, this technique has never before been used for releasing active ingredients to the skin.

The method of making the garment of the present invention involves chemically binding the binding agent molecules to the durable binding sites and then, under conditions which are different from skin conditions, chemically binding the active ingredient molecules to the semi-durable binding sites of the binding agent. Although it is contemplated that multiplicities of the durable and semi-durable chemical binding sites will be provided, it is not essential that every single one of the durable binding sites receive one of the binding agent molecules nor that every single one of the semi-durable binding sites receive an active ingredient molecule. It is sufficient that enough of the active ingredient molecules be present to treat the skin either cosmetically or physiologically, by release of the active ingredient molecules to the skin. It is understood thus that many more durable and semi-durable chemical bonding sites may be present but only those to which the binding agent is attached and to which, in turn, the active ingredient molecule is attached, are considered for the present disclosure.

The term "active ingredient molecule" is also meant to include both cosmetic substances and physiological substances. Skin moisturizers for example may qualify as the active ingredient, as well as chemicals which can alleviate skin conditions such as rashes and also anti-cellulite ingredients such as those disclosed in connection with the preferred embodiment of the present invention.

Figure 3A:
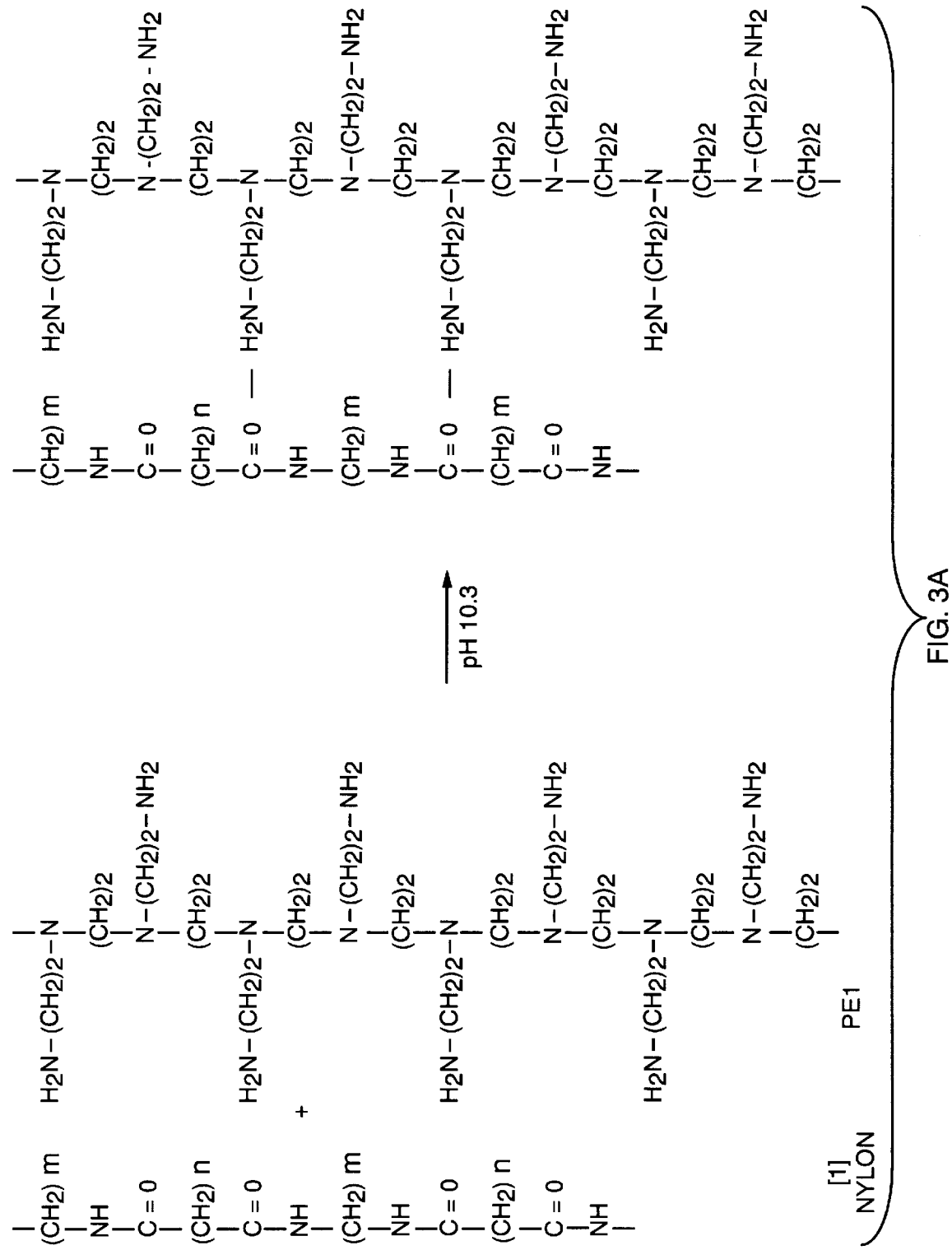
FIGS. 3A and 3B show the chemical scheme for the preferred embodiment of the present invention.
Figure 3B:
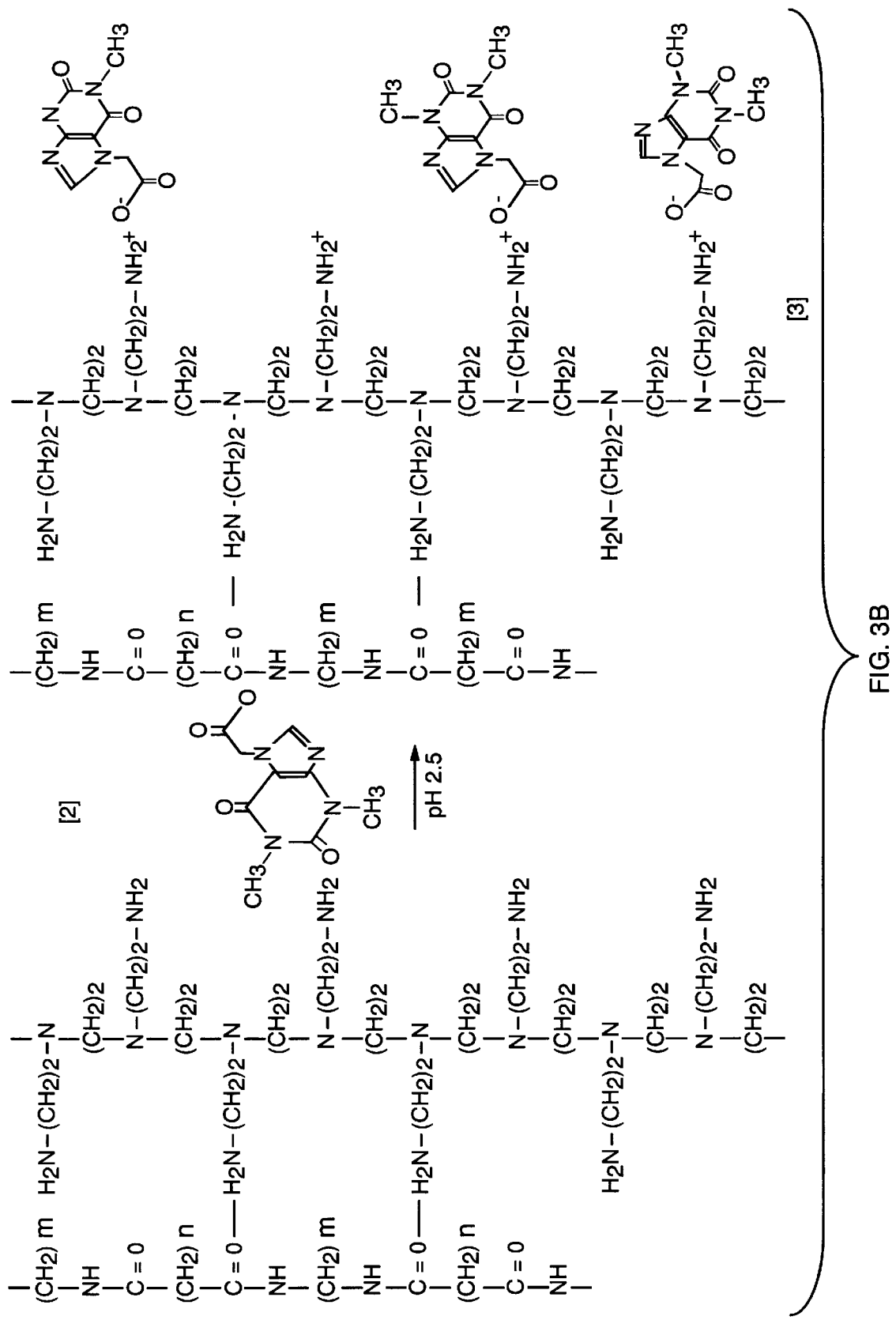

Turning now to FIG. 3A, the chemical scheme of the present invention is disclosed. Compound [1] is the nylon chain which has been treated with polyethylenimine (PEI) to connect the PEI by durable chemical bonds at the nitrogen sites along the nylon chain at pH 10.3. The resulting treated nylon is combined with active ingredient molecule [2], theophylline acetate (THA), as shown in FIG. 3B and at pH 2.5 to create the chain [3] where the THA is attached at ionic bonds, forming semi-durable bonds along the nylon chain.

The Polyethylaminine (PEI) is a weak polybasic aliphatic amine that, among all the synthetic polymers, shows the highest concentration of aminogroups per unit. PEI is used for coating onto the nylon support of stockings in order to prepare pantyhose with lipolytic activity.

The PEI dissolved in distilled water shows an alkali pH (10.3) and it is strongly absorbed by the nylon via electrostatic and H-bonds between the carbonilic groups of the nylon structure and the aminic groups of PEI. In acidic solution (pH 2.5) the PEI has positive charges able to couple by ionic bonds with the amon theophylline acetate.

The present invention uses a complex of theophylline and silantriol chemically bonded through the linking compound (PEI) to nylon which has been fabricated into pantyhose. The theophylline-silantriol complex is released from the binding, or linking compound by a combination of water and pH. The nylon can be reloaded with theophylline as often as desired.

Figure 4:
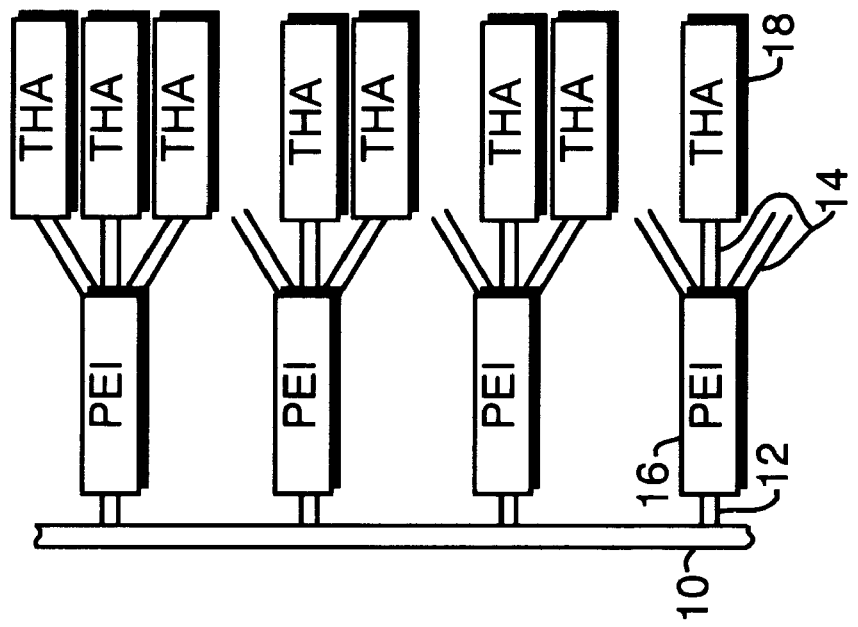
FIG. 4 is a schematic illustration of the chemical make-up of a product according to the present invention.

Nylon is a linear compound that contains a nitrogen atom at every six carbon atom. FIG. 4 schematically illustrates a nylon chain 10. Using a compound known as polyethylenimine (PEI) (10) it is possible to make a direct link to nylon at specific durable chemical sites 12. The binding of PEI to nylon provides three additional binding sites for the attachment of theophylline. Theophylline is used not as plain theophylline but as theophylline acetate (THA). The presence of the acetate molecule allows the binding of the theophylline to the PEI in a ratio of 1 molecule of PEI to three molecules of THA 18 at bonds 14.

Complex of THA with Silantriol

Silantriol is a silica based compound that has been shown to increase the penetration of certain chemical compounds that are not easily passed into the skin. Silantriol can be complexed with theophylline acetate at a ph of 5. The method involves adding the silantriol in increments to a solution of theophylline acetate and adjusting the pH to 5.5. After adding the silantriol the pH must again be adjusting to a lower level in order to bind the THA-silantriol to the nylon.

Binding of the Ingredients to the Nylon

Step One

The pantyhose are washed in distilled water twice and damped dried (spinning).

Step Two

They are then placed in a solution of PEI for 30 minutes with constant agitation at 10.3 pH. They are removed, washed twice in deionized water and damp dried.

Step Three

They are then placed in solution of be THA-silantriol complex for 3 hours at 2.5 pH with constant agitation. They are removed, washed twice in deionized water and dried.

The compound is stable indefinitely in the dry state.

Release of THA-Silantriol Complex from the Nylon

Part of this invention relates to the releasing mechanism of freeing the THA-silantriol complex from the pantyhose to reach the skin. The nylon binding molecule is permanently fixed to the nylon in the pantyhose. The bond between the PEI and the THA is a pH sensitive bond that will break as the pH goes up. Skin pH is 5.5 which is above the pH needed for bonding THA to the nylon, so it will release slowly onto the skin. This is a controlled release and is a critical part of the invention. As the nylon stretches with the movement of the wearer more THA complex is released. The three elements that combine to release the THA complex are (1) skin pH (2) skin moisture (3) skin heat (due to friction and/or body heat).

Distinctions and advantages of the invention includes:

1. A compound with a permanent chemical bond is attached to hose material, which allow other active ingredients to be applied to it. This is called the "chemical hook".
2. The active ingredient is attached to the chemical hook, not to the hose material, e.g. nylon, per se.
3. The chemical hook permits an amplification of the sites available for binding. For example, one hook will bind three THA complex molecules.
4. The chemical hook allows binding of many possible active ingredients.
5. The chemical hook may be loaded with active material such as the THA complex as desired.
6. The release of this active is controlled by a combination of pH, moisture and friction induced heat.

Experimental Data Summary

We have about 12 individuals who have used the pantyhose with good results. One documented person was studied with photographs, ultrasound and clinical evaluation and showed a reduction of thigh diameter of 1 inch in 30 days.

Binding of theophylline-complex and release rating have been done extensively to show that the release is controlled. The active compound remains on the pantyhose for a minimum of 3 days with continuing sustained release. The pantyhose can be released at home with a simple rinse or wash solution.

Keys to understanding the present invention are:

The nylon is not chemically altered but supplied with an amplification compound to which physiologically active compounds may be added.

The system allows for a controlled release of the active by using specific pH values. The pantyhose may be recharged at will.

This is not a mechanical sprayed on or pressed-on or particle application.

It is specific chemical binding of a controlled releasing mechanism which is bonded to the nylon and be active bonded to the releasing mechanism.

Description of the Anti-cellulite Product Tested

Nylon thread is knitted into a standard pair of pantyhose and dyed. The pantyhose is then washed in water at room temperature with moderated agitation, rinsed and washed again. After spin drying the damp pantyhose is placed in a 1% aqueous solution of polyethylenimine (PEI) for 30 minutes with continuous agitation and at 10.3 pH which was found to be critical. After removing the pantyhose from the PEI they are rinsed twice in water and spin dried. The damp pantyhose to which the binding agent or PEI hook is durably bonded by covalent bonds, is placed in a 0.2% solution of 1,3 dimethyl xanthine theophylline containing 0.1% to 0.5% of ilantril for 3 hours with agitation. At the end of the three hours the pantyhose is rinsed twice and dried in a force hot air drier. The theophylline is chemically bonded by ionic bond as the semi-durable bond, to the PEI which is bonded to the nylon. All test products were prepared at the same time.

Testing Procedure

One female subject with moderate to severe cellulite was instructed to wear the treated anti-cellulite pantyhose for eight hours a day. The pantyhose was charged every 4th day and a new pair was supplied, so that each pair represented three full days of wear. Each night the pantyhose was washed in mild detergent and water. The subject reported to the laboratory each week for cirumferencial measurements of her thighs, three view photographs, i.e. anterior, posterior and laterals. Ultrasound measurements and clinical evaluation were made as well.

Results

Figure 2:
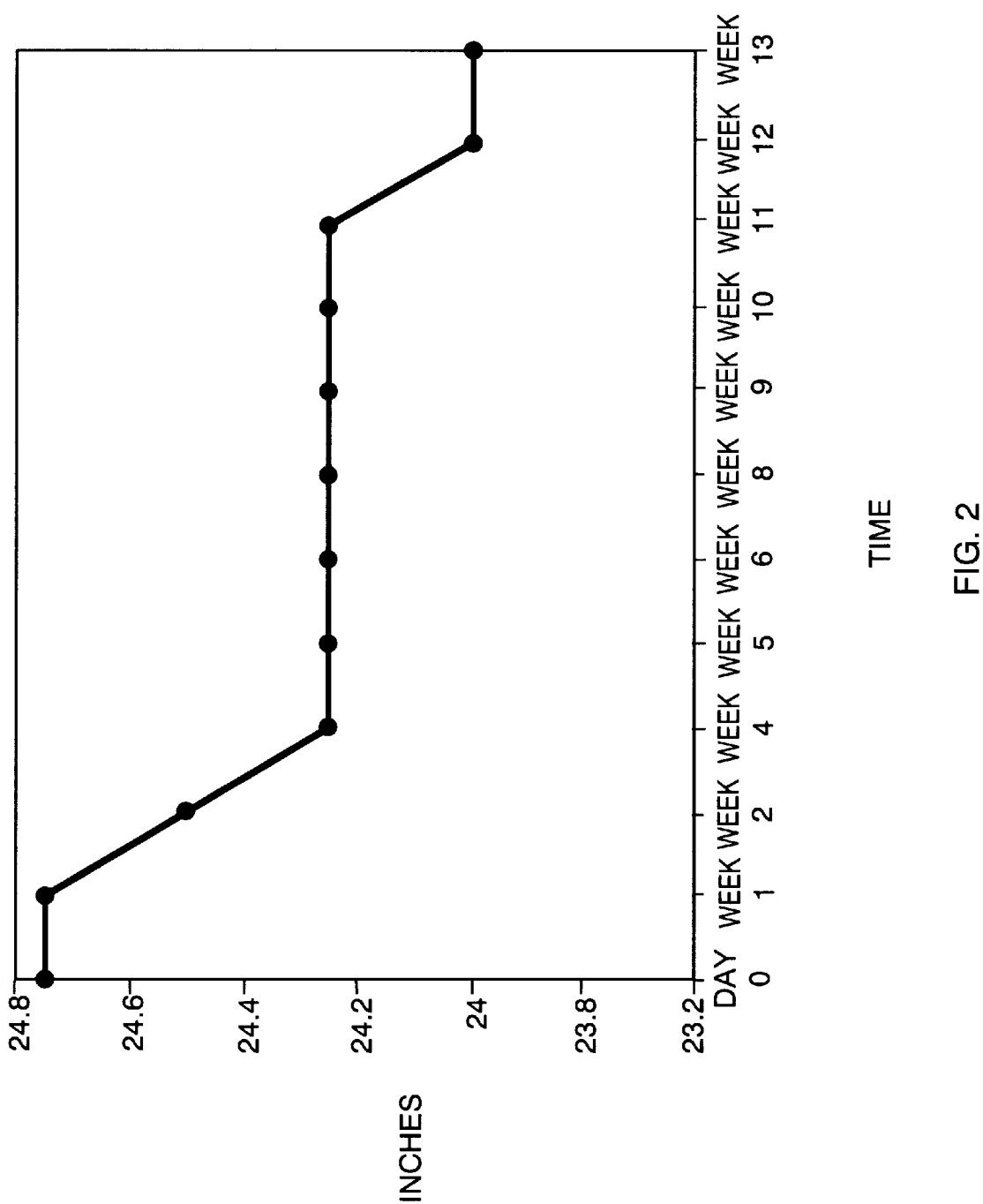
FIG. 2 is a graph similar to FIG. 1 showing the same results for the right thigh.

The results show a one inch decrease in circumference of both the right and left thighs over four weeks. The study continued for a total of twelve weeks with a further decrease in the thigh circumference of about 0.5 inches. FIGS. 1 and 2 graph the thigh circumferences observed.

The thighs appeared smoother, there was less irregularity of the surface. The subject stated that her formerly tight jeans "felt baggy and loose".

The photographs showed a decrease in the diameter of the buttocks with less fatty tissue on the hips. The skin felt firmer and smoother.

Conclusions:

Based on this initial study the following conclusions can be made:

1. The anti-cellulite pantyhose is effective in reducing the circumference of the thighs by 1 inch in four weeks
2. The anti-cellulite pantyhose is effective in reducing the fatty deposits around the buttocks.
3. The anti-cellulite pantyhose is effective in reducing the irregular surface of the thighs.
4. The anti-cellulite pantyhose is effective in producing smoother, firmer thighs.
5. The anti-cellulite pantyhose is effective in reshaping the appearance of the thighs and buttocks.

While specific embodiments of the invention have been shown and described in detail to illustrate the application of the principles of the invention, it will be understood that the invention may be embodied otherwise without departing from such principles.

What is claimed is:

1. A garment for treating skin of a wearer with an active ingredient, comprising:
    (a) a knitted garment material selected from the group consisting of one of nylon and polyester adapted to be worn tightly against the skin and having a multiplicity of durable chemical binding sites;
    (b) a binding agent molecule selected from one of the polyimines which are the durable binding sites, each binding agent molecule having at least one semi-durable chemical binding site which can be broken by at least one of the skin conditions of skin pH, skin moisture and skin heat; and
    (c) an active ingredient selected from one of theophylline and silantriol being bound to each semi-durable chemical binding site so that the active ingredient remains chemically bound to the garment when the garment is not worn and so that the active ingredient is released to the skin when the garment is being worn, and the semi-durable binding sites on the agent molecule are exposed to at least one of skin pH, skin moisture and skin heat serving to break the chemical bonds between the active ingredient and the binding agent molecules.

2. A garment according to claim 1, wherein the binding agent molecules are generally bound by covalent bonds at the durable chemical bonding sites.

3. A garment according to claim 2, wherein the active ingredient molecules are bound to the binding agent molecules by ionic bonds forming the semi-durable chemical binding sites.

4. A garment according to claim 3, wherein the garment material is pantyhose material.

5. A garment according to claim 1, wherein the binding agent is polyethylenimine.

6. A garment according to claim 5, wherein the primary active ingredient is theophylline.

7. A garment according to claim 6, wherein the theophylline is theophylline acetate.

8. A garment according to claim 7, wherein the active ingredient molecule includes the silanol silantriol bound to the theophylline acetate.

9. A method of making a knitted garment for treating skin of a wearer with an active ingredient, the garment being selected from the group consisting of one of nylon and polyester having a multiplicity of durable chemical binding sites and being for a tightly fitting garment that lies against the skin, the method comprising:
    (a) chemically binding to the durable chemical binding sites, binding agent molecules, each binding agent molecule selected from one of the polyimines having at least one semi-durable chemical binding site which can be broken by a skin condition comprising at least one of skin pH, skin moisture and skin heat; and
    (b) chemically binding to the semi-durable binding sites, an active ingredient molecules selected from one of theophylline and silantriol under conditions different from the skin conditions so that the active ingredient is chemically bound to the garment when the garment is not being worn and so that the active ingredient is released to the skin when the garment is being worn and the semi-durable binding sites on the agent molecule are exposed to at least one of skin pH, skin moisture and skin heat serving to break the bonds between the active ingredient molecules and the binding agent molecules.

10. A method according to claim 9, including binding the binding agent molecules to the garment material by covalent bonds forming the durable binding sites.

11. A method according to claim 10, including binding the active ingredient molecules to the active ingredient molecules by ionic bonds forming the semi-durable binding sites.

12. A method according to claim 11, including chemically binding the active ingredient molecule to the semi-durable binding sites while under a pH of lower than 5 pH, and the skin condition for breaking the ionic bond comprising a pH of at least 5 pH.

13. A method according to claim 9, including providing nylon as the hose material, providing polyethylinimine as the binding agent and providing theophylline as the primary active ingredient.

14. A method according to claim 13, including providing theophylline acetate as the active ingredient.

15. A method according to claim 14, including providing theophylline acetate bound to the silanol silantriol as the active ingredient.

16. A method according to claim 15, including chemically bonding the binding agent molecules to the durable chemical binding sites while at a pH of about 4.2.

17. A method for treating skin with an active ingredient, using a knitted garment made of material selected from the group consisting of nylon and polyester and having a multiplicity of durable chemical binding sites, a binding agent molecule selected from one of the polyimines, which are chemically bound to each of the durable binding sites, each binding agent molecule having at least one semi-durable chemical binding site which can be broken by a skin condition of at least one of skin pH, skin moisture and skin heat, and an active ingredient molecule selected from one of theophylline and silantriol which are bound to each semi-durable chemical binding site so that the active ingredient is chemically bound to the garment when the garment is not worn, the method comprising:

(a) covering the skin closely with the garment for exposing the garment to the skin pH, to the skin moisture and to the skin heat; and (b) maintaining the covering of the skin for sufficient time so that the active ingredient is released to the skin by the semi-durable binding sites being exposed to at least one of the skin pH, the skin moisture and the skin heat to break the bonds between the active ingredient molecules and the binding agent molecules.

18. A method according to claim 17, including recharging the garment with active ingredient by chemically binding added active ingredient to the semi-durable chemical binding sites being effected under conditions different from those skin conditions which provide active ingredient release, after an initial treatment of using the garment and an initial releasing the active ingredients to the skin.

19. A method according to claim 17, including treating cellulite, with the binding agent being polyethylineimine, and the active ingredient being theophylline.

20. A method according to claim 19, wherein the active ingredient is theophylline acetate.

21. A method according to claim 20, wherein the active ingredient and theophylline acetate-silantriol complex.

22. A method according to claim 21, including breaking the semi-durable bonding sites by a skin pH of at most 5 pH.

23. A method according to claim 22, wherein the garment comprises pantyhose, the method including covering at least the legs of a wearer with the hose.

* * * * *